United States Patent
Zhu

(10) Patent No.: US 9,617,370 B2
(45) Date of Patent: Apr. 11, 2017

(54) POLYURETHANE USEFUL FOR ORTHOPEDICS EXTERNAL FIXING SYSTEM IN COMPLEX ENVIRONMENT AND PREPARATION METHOD THEREOF

(71) Applicant: Xieping Zhu, Shanghai (CN)

(72) Inventor: Xieping Zhu, Shanghai (CN)

(*) Notice: Subject to any disclaimer, the term of this patent is extended or adjusted under 35 U.S.C. 154(b) by 0 days.

(21) Appl. No.: 14/799,550

(22) Filed: Jul. 14, 2015

(65) Prior Publication Data

US 2015/0315328 A1   Nov. 5, 2015

Related U.S. Application Data

(63) Continuation-in-part of application No. 13/814,503, filed as application No. PCT/CN2010/000785 on Jun. 2, 2010, now abandoned.

(30) Foreign Application Priority Data

Jun. 2, 2009   (CN) .......................... 2009 1 0052379

(51) Int. Cl.
| | |
|---|---|
| C08G 18/18 | (2006.01) |
| C08K 3/26 | (2006.01) |
| C08K 3/36 | (2006.01) |
| C08G 18/48 | (2006.01) |
| C08G 18/76 | (2006.01) |
| C08G 18/20 | (2006.01) |
| C08K 3/30 | (2006.01) |
| C08G 18/10 | (2006.01) |
| C08L 75/08 | (2006.01) |
| C08J 9/14 | (2006.01) |
| A61L 15/12 | (2006.01) |
| C08G 101/00 | (2006.01) |

(52) U.S. Cl.
CPC .......... *C08G 18/1816* (2013.01); *A61L 15/12* (2013.01); *C08G 18/20* (2013.01); *C08G 18/2063* (2013.01); *C08G 18/2081* (2013.01); *C08G 18/4829* (2013.01); *C08G 18/4883* (2013.01); *C08G 18/7664* (2013.01); *C08G 18/7671* (2013.01); *C08J 9/144* (2013.01); *C08K 3/26* (2013.01); *C08K 3/36* (2013.01); *C08G 2101/0025* (2013.01); *C08G 2101/0083* (2013.01); *C08J 2203/142* (2013.01); *C08J 2375/04* (2013.01); *C08K 2003/265* (2013.01); *C08K 2003/3045* (2013.01)

(58) Field of Classification Search
IPC ................. A61L 15/12; C08J 9/144,2203/142, 2375/04; C08K 3/26, 3/36, 2003/3045, 2003/265; C08L 75/08, 67/04; C08G 18/20, 18/7664, 18/4883, 18/2081, 18/1816, 18/4829, 18/48, 18/76, 18/7671, 18/2063, 2101/0083, 18/10
See application file for complete search history.

(56) References Cited

U.S. PATENT DOCUMENTS

| | | | | |
|---|---|---|---|---|
| 5,984,884 | A * | 11/1999 | Alvarez | ............... A61F 13/04 206/440 |
| 2002/0147420 | A1* | 10/2002 | Morris | ................ A61F 13/04 602/8 |
| 2002/0160684 | A1* | 10/2002 | Morris | ................ A61F 13/04 442/415 |

* cited by examiner

*Primary Examiner* — Rabon Sergent
(74) *Attorney, Agent, or Firm* — Matthias Scholl, PC; Matthias Scholl

(57) ABSTRACT

A polyurethane used for orthopedics external fixing system in complex environment is obtained by reaction of mixture of polyether polyol with modified isocyanate in the weight ratio of 1:0.6-0.75. The modified isocyanate is obtained by reaction of polyphenylene polymethylene isocyanate with polyether glycol. The components and corresponding weight percent amounts of the mixture of polyether polyol are as follows: 60-65% polyether polyol; 0.3-1% catalyst; 0.1-2% foam stabilizer; 0.1-2% or 3-20% foaming agent; 25-40% filler and 0.5-2% functional auxiliary agent. The method of producing the polyurethane is also provided.

10 Claims, No Drawings

POLYURETHANE USEFUL FOR ORTHOPEDICS EXTERNAL FIXING SYSTEM IN COMPLEX ENVIRONMENT AND PREPARATION METHOD THEREOF

CROSS-REFERENCE TO RELATED APPLICATIONS

This application is a continuation-in-part of U.S. application Ser. No. 13/814,503, filed on Feb. 5, 2013, now pending, which is a National Stage Appl. filed under 35 USC 371 of International Patent Application No. PCT/CN2010/000785 with an international filing date of Jun. 2, 2010, designating the United States, and further claims priority benefits to Chinese Patent Application No. 200910052379.X filed Jun. 2, 2009. Inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

FIELD OF THE INVENTION

The invention relates to a polymer material and a preparation method thereof, and more particularly to a polyurethane for an external fixation system for orthopedics and a method for preparing the same.

BACKGROUND OF THE INVENTION

Chinese Patent Application No. 200810038254.7, titled as a new external fixation system for orthopedics, a using method thereof, and a polyurethane for the fixation system, has disclosed a polyurethane for an external fixation system for orthopedics. However, in poor conditions, for example, in the field at a low temperature, where no hospitals are available, and the temperature is about 5-15° C., the fixation system cannot be hardened by the polyurethane; whereas in the temperature of 25-30° C., the hardening of the fixation system is too fast and produces too much heat.

SUMMARY OF THE INVENTION

In view of the above-described problems, it is one objective of the invention to provide a polyurethane for an external fixation system for orthopedics. The polyurethane can effectively overcome problems resulting from hardening and heat production.

It is another objective of the invention to provide a method for preparing the polyurethane for an external fixation system for orthopedics.

Technical scheme of the invention is as follows:

A polyurethane for an external fixation system for orthopedics, is a polyether polyurethane which is prepared by using a polyether polyol mixture and a modified isocyanate as raw materials according to a weight ratio of 1:0.6-0.75. In the polymerization reaction of the polyether polyol and the modified isocyanate, reaction occurs between the hydroxyl groups within the polyether polyol and the isocyanate groups within the modified isocyanate to form the polyether polyurethane having urethane groups.

The reaction between the hydroxyl groups within the polyether polyol and the isocyanate groups within the modified isocyanate may be represented as follows:

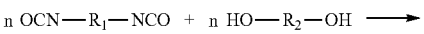

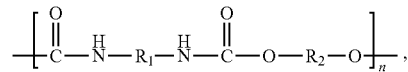

in which $R_1$ represents the part of the modified isocyanate molecule except two isocyanate groups at the terminals of the molecular chain of the modified isocyanate molecule, and $R_2$ represents the part of the polyether polyol molecule except two hydroxyl groups therein.

The polyether polyol mixture comprises ingredients in the following weight percentages with respect to the polyether polyol mixture:

| | |
|---|---|
| the polyether polyol | 60-65 wt. %, |
| a catalyst | 0.3-1 wt. %, |
| a foam stabilizer | 0.1-2 wt. %, |
| a foaming agent | 0.1-2 wt. % or 3-20 wt. %, |
| a filler | 25-40 wt. %, and |
| a functional additive | 0.5-2 wt. %. |

The polyether polyol is selected from the following compounds:

a) a first polyether polyol represented by a formula of

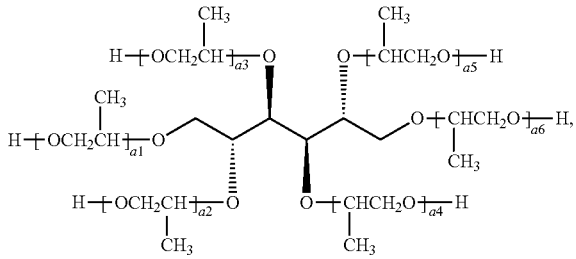

in which a1, a2, a3, a4, a5, and a6 are integers, and the sum of a1, a2, a3, a4, a5, and a6 is from 7 to 15;

b) a second polyether polyol represented by a formula of

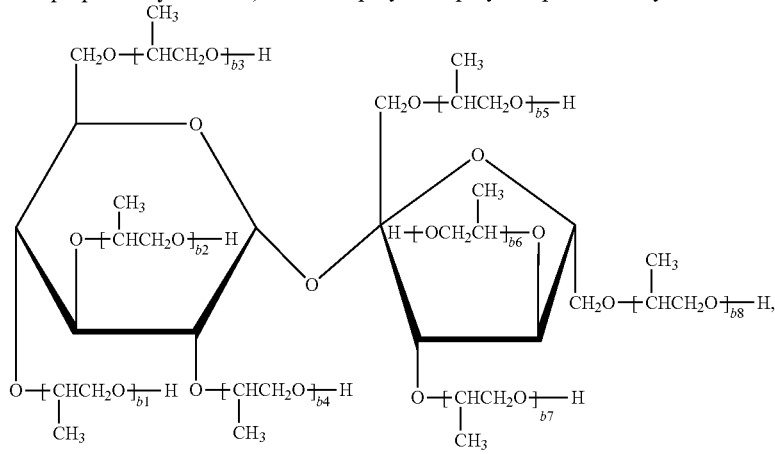

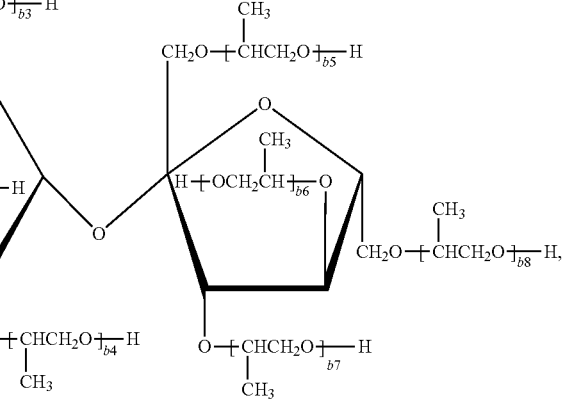

in which b1, b2, b3, b4, b5, b6, b7, and b8 are integers, and the sum of b1, b2, b3, b4, b5, B6, b7, and b8 is from 7 to 15;

c) a third polyether polyol represented by a formula of

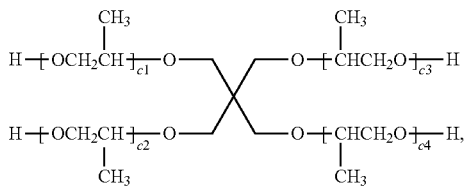

in which c1, c2, c3, and c4 are integers, and the sum of c1, c2, c3, and c4 is from 7 to 15; or d) a mixture of more than one of the first polyether polyol, the second polyether polyol, and the third polyether polyol.

The modified isocyanate may have a formula of

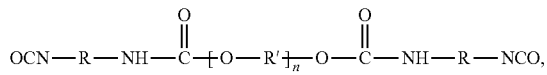

in which R is a functional group containing methylene groups and phenylene groups, and R' can be —$CH_2CH_2$—.

The modified isocyanate is prepared by using a polyphenylene polymethylene isocyanate (e.g., 4,4'-diphenylmethane diisocyanate (MDI)) and the polyether glycol as raw materials. The polyphenylene polymethylene isocyanate is represented by a formula of

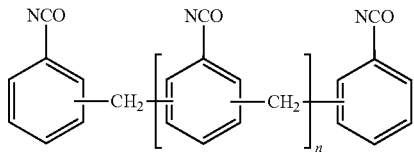

in which, n represents 0, 1, 2, or 3.

The catalyst in the polyether polyol mixture is selected from dimethylcyclohexylamine, dimethyl ethanolamine, or triethylene diamine.

The foam stabilizer in the polyether polyol mixture is a silicone stabilizer.

The foaming agent in the polyether polyol mixture is water or $CH_3CCl_2F$.

If the foaming agent is water, the content of the foaming agent is 0.1-2 wt. % of the polyether polyol mixture; and if the foaming agent is $CH_3CCl_2F$, the content of the foaming agent is 3-20 wt. % of the polyether polyol mixture.

The filler in the polyether polyol mixture is calcium carbonate, or barium sulfate.

The functional additive in the polyether polyol mixture is silica.

A method for prepare the polyurethane, comprises steps as follows:

a) mixing the polyphenylene polymethylene isocyanate and the polyether glycol, and allowing for reaction at a temperature of 70-90° C. to obtain the modified isocyanate;

b) mixing the polyether polyol, the catalyst, the foam stabilizer, the foaming agent, the filler, and the functional additive according to a certain ratio to obtain the polyether polyol mixture; and c) mixing the polyether polyol mixture from step b) and the modified isocyanate from step a) according to a ratio of 1:0.6-0.75 to obtain the polyurethane.

Raw materials used in the preparation are all commercial products.

The polyurethane of the invention can be used at a temperature of 5-15° C.

The polyurethane of the invention can be used at a temperature of 25-30° C.

An optimal temperature for using the polyurethane of the invention is 21-25° C.

Advantages of the invention are summarized as follows:

The polyurethane of the invention can be used at a temperature of 5-15° C., and can fix fracture regions that are difficult to fix by plasters. The polyurethane has sufficient rigidity and intensity. X-ray can penetrate the polyurethane, so that the situation of the fracture region can be known. Besides, the polyurethane is sanitary and is convenient to expose the skin to oxygen; medical personnel can easily take off the polyurethane to clean and process the skin on the fracture region. Furthermore, the polyurethane has a much lower cost than metal stents, a much better fixation effect than polymer bandages or plasters, and does not result in infections or secondary hurts. Finally, when the polyurethane is attached to the skin, a temperature of a heat production is no higher than 38° C., and different shaping durations can be selected to avoid inducing cardiovascular diseases.

DETAILED DESCRIPTION OF THE EMBODIMENTS

To further illustrate the invention, experiments detailing a polyurethane and a method for preparing the same are described below. It should be noted that the following examples are intended to describe and not to limit the invention.

Example 1

Preparation of a modified isocyanate: a polyphenylene polymethylene isocyanate and a polyether glycol were mixed, and a reaction was carried out at a temperature of 70-90° C. to obtain the modified isocyanate.

Preparation of a polyether polyol mixture: 60 weight parts of a polyether polyol, 0.5 weight part of triethylene diamine, 1 weight part of a silicone stabilizer, 0.5 weight part of water, 37 weight parts of calcium carbonate, and 1 weight part of silica were collected and mixed to obtain the polyether polyol mixture.

Preparation of a polyurethane: the polyether polyol mixture and the modified isocyanate are mixed according to a ratio of 1:0.6 to obtain the polyurethane.

Example 2

Preparation of a modified isocyanate is the same as that of Example 1.

Preparation of a polyether polyol mixture: 61 weight parts of a polyether polyol, 1 weight part of triethylene diamine, 2 weight parts of a silicone stabilizer, 0.1 weight part of water, 35.4 weight parts of calcium carbonate, and 0.5 weight part of silica were collected and mixed to obtain the polyether polyol mixture.

Preparation of a polyurethane: the polyether polyol mixture and the modified isocyanate are mixed according to a ratio of 1:0.65 to obtain the polyurethane.

Example 3

Preparation of a modified isocyanate is the same as that of Example 1.

Preparation of a polyether polyol mixture: 62 weight parts of a polyether polyol, 0.3 weight part of triethylene diamine, 2 weight parts of a silicone stabilizer, 2 weight parts of water, 33 weight parts of calcium carbonate, and 0.7 weight part of silica were collected and mixed to obtain the polyether polyol mixture.

Preparation of a polyurethane: the polyether polyol mixture and the modified isocyanate are mixed according to a ratio of 1:0.65 to obtain the polyurethane.

Example 4

Preparation of a modified isocyanate is the same as that of Example 1.

Preparation of a polyether polyol mixture: 63 weight parts of a polyether polyol, 1 weight part of dimethyl ethanolamine, 0.5 weight part of a silicone stabilizer, 1 weight part of water, 33 weight parts of calcium carbonate, and 1.5 weight parts of silica were collected and mixed to obtain the polyether polyol mixture.

Preparation of a polyurethane: the polyether polyol mixture and the modified isocyanate are mixed according to a ratio of 1:0.7 to obtain the polyurethane.

Example 5

Preparation of a modified isocyanate is the same as that of Example 1.

Preparation of a polyether polyol mixture: 64 weight parts of a polyether polyol, 0.5 weight part of dimethylcyclohexylamine, 1.5 weight parts of a silicone stabilizer, 7 weight parts of $CH_3CCl_2F$, 25 weight parts of barium sulfate, and 2 weight parts of silica were collected and mixed to obtain the polyether polyol mixture.

Preparation of a polyurethane: the polyether polyol mixture and the modified isocyanate are mixed according to a ratio of 1:0.75 to obtain the polyurethane.

Example 6

Preparation of a modified isocyanate is the same as that of Example 1.

Preparation of a polyether polyol mixture: 65 weight parts of a polyether polyol, 1 weight part of dimethylcyclohexylamine, 1.2 weight parts of a silicone stabilizer, 1 weight part of water, 30 weight parts of barium sulfate, and 1.8 weight parts of silica were collected and mixed to obtain the polyether polyol mixture.

Preparation of a polyurethane: the polyether polyol mixture and the modified isocyanate are mixed according to a ratio of 1:0.63 to obtain the polyurethane.

Example 7

Preparation of a modified isocyanate is the same as that of Example 1.

Preparation of a polyether polyol mixture: 60 weight parts of a polyether polyol, 0.3 weight part of dimethylcyclohexylamine, 0.2 weight part of a silicone stabilizer, 14 weight parts of $CH_3CCl_2F$, 25 weight parts of barium sulfate, and 0.5 weight part of silica were collected and mixed to obtain the polyether polyol mixture.

Preparation of a polyurethane: the polyether polyol mixture and the modified isocyanate are mixed according to a ratio of 1:0.68 to obtain the polyurethane.

The invention claimed is:

1. A polyurethane for an external fixation system for orthopedics, the polyurethane being a polyether polyurethane prepared by a polymerization reaction using a polyether polyol mixture and a modified isocyanate as raw materials, the polyether polyol mixture comprising a polyether polyol, the polyether polyol comprising hydroxyl groups, the modified isocyanate comprising isocyanate groups at terminals of a molecular chain of the modified isocyanate, and the polymerization reaction being a reaction between the hydroxyl groups and the isocyanate groups to form urethane groups, wherein the polyether polyol mixture and the modified isocyanate as raw materials in the polymerization reaction have a weight ratio of 1:0.6-1:0.75;

the polyether polyol mixture comprises ingredients in the following weight percentages with respect to the polyether polyol mixture:

| | |
|---|---|
| the polyether polyol | 60-65 wt. %, |
| a catalyst | 0.3-1 wt. %, |
| a foam stabilizer | 0.1-2 wt. %, |
| a foaming agent | 0.1-2 wt. % or 3-20 wt. %, |
| a filler | 25-40 wt. %, and |
| a functional additive | 0.5-2 wt. %; | wherein the polyether polyol is selected from the following compounds:

a) a first polyether polyol represented by a formula of

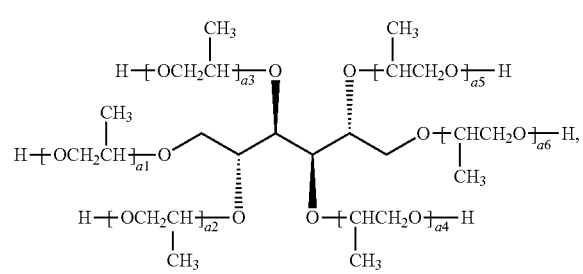

wherein a1, a2, a3, a4, a5, and a6 are integers, and a sum of a1, a2, a3, a4, a5, and a6 is from 7 to 15;

b) a second polyether polyol represented by a formula of

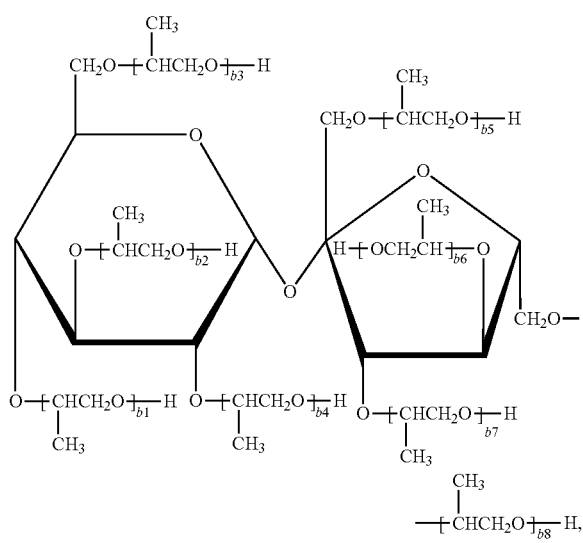

wherein b1, b2, b3, b4, b5, b6, b7, and b8 are integers, and a sum of b1, b2, b3, b4, b5, b6, b7, and b8 is from 7 to 15;

c) a third polyether polyol represented by a formula of

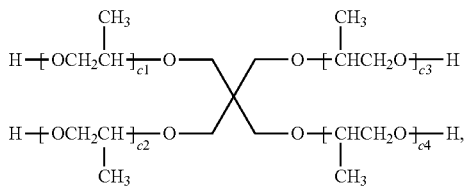

wherein c1, c2, c3, and c4 are integers, and a sum of c1, c2, c3, and c4 is from 7 to 15; or d) a mixture of two or three compounds selected from the group consisting of the first polyether polyol, the second polyether polyol, and the third polyether polyol; and the modified isocyanate is prepared from polymerization reaction of polyether glycol with diphenylmethane diisocyanate (MDI) or with a polyphenylene polymethylene isocyanate.

2. The polyurethane of claim 1, wherein the polyphenylene polymethylene isocyanate is represented by a formula of

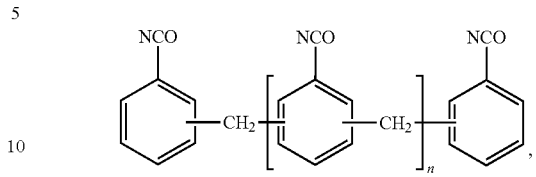

wherein n represents 1, 2, or 3.

3. The polyurethane of claim 1, wherein the modified isocyanate is prepared by using the polyphenylene polymethylene isocyanate and polyether glycol as raw materials.

4. The polyurethane of claim 1, wherein the catalyst in the polyether polyol mixture is selected from dimethylcyclohexylamine, dimethyl ethanolamine, or triethylene diamine.

5. The polyurethane of claim 1, wherein the foam stabilizer in the polyether polyol mixture is a silicone stabilizer.

6. The polyurethane of claim 1, wherein the foaming agent in the polyether polyol mixture is water or $CH_3CCl_2F$.

7. The polyurethane of claim 6, wherein
when the foaming agent is water, the content of the foaming agent is 0.1-2 wt. % of the polyether polyol mixture; and
when the foaming agent is $CH_3CCl_2F$, the content of the foaming agent is 3-20 wt. % of the polyether polyol mixture.

8. The polyurethane of claim 1, wherein the filler in the polyether polyol mixture is calcium carbonate or barium sulfate.

9. The polyurethane of claim 1, wherein the functional additive in the polyether polyol mixture is silica.

10. A method for preparing the polyurethane of claim 3, comprising:
a) mixing the polyphenylene polymethylene isocyanate and the polyether glycol, and allowing for reaction at a temperature of 70-90° C. to obtain the modified isocyanate;
b) mixing the polyether polyol, the catalyst, the foam stabilizer, the foaming agent, the filler, and the functional additive according to a certain ratio to obtain the polyether polyol mixture; and
c) mixing the polyether polyol mixture from step b) and the modified isocyanate from step a) at a weight ratio of 1:0.6-0.75 to obtain the polyurethane.

* * * * *